(12) United States Patent
Scott et al.

(10) Patent No.: US 7,135,007 B2
(45) Date of Patent: Nov. 14, 2006

(54) COMPRESSION GARMENTS AND RELATED METHODS

(75) Inventors: Edwin R. Scott, Cedar Hills, UT (US); Annerose Zorn, Gates Mills, OH (US)

(73) Assignee: Julius Zorn, Inc., Cuyahoga Falls, OH (US)

( * ) Notice: Subject to any disclaimer, the term of this patent is extended or adjusted under 35 U.S.C. 154(b) by 20 days.

(21) Appl. No.: 10/719,407

(22) Filed: Nov. 21, 2003

(65) Prior Publication Data
US 2005/0113729 A1    May 26, 2005

(51) Int. Cl.
*A61L 15/00*    (2006.01)
(52) U.S. Cl. .......................... 602/75; 602/76
(58) Field of Classification Search ............ 602/61–63, 602/75, 5, 23, 21; 606/201, 204, 206; 601/132, 601/134; 128/846, 878
See application file for complete search history.

(56) References Cited

U.S. PATENT DOCUMENTS

| | | |
|---|---|---|
| 800,467 A | 9/1905 | Myers |
| 814,795 A | 3/1906 | Myers |
| 2,533,504 A | 12/1950 | Poor |
| 2,781,041 A | 2/1957 | Weinberg |
| 2,823,668 A | 2/1958 | Court et al. |
| 3,186,405 A | 6/1965 | Bailey et al. |
| 3,454,010 A | 7/1969 | Lilligren et al. |
| 3,561,435 A | 2/1971 | Nicholson |
| 3,845,769 A | 11/1974 | Shaw |
| 3,850,167 A | 11/1974 | Seeley |
| 3,856,008 A | 12/1974 | Fowler et al. |
| 3,888,242 A | 6/1975 | Harris et al. |
| 3,892,239 A * | 7/1975 | Masso Remiro ............ 604/312 |
| 3,975,929 A | 8/1976 | Fregeolle |
| 4,150,422 A | 4/1979 | Peralta et al. |
| 4,157,713 A | 6/1979 | Clarey |
| 4,186,738 A | 2/1980 | Schleicher et al. |
| 4,215,687 A | 8/1980 | Shaw |
| 4,315,504 A | 2/1982 | Drennan et al. |
| 4,338,923 A | 7/1982 | Gelfer et al. |
| 4,369,588 A | 1/1983 | Berguer |
| 4,370,975 A | 2/1983 | Wright |
| 4,374,518 A | 2/1983 | Villanueva |
| 4,383,342 A | 5/1983 | Forster |
| 4,421,110 A | 12/1983 | DeLisle et al. |
| 4,476,857 A * | 10/1984 | Levine ........................ 602/20 |
| 4,573,456 A | 3/1986 | Spann |
| 4,738,249 A | 4/1988 | Linman et al. |
| 4,791,041 A | 12/1988 | Aoki et al. |
| 4,945,903 A | 8/1990 | Alper |

(Continued)

FOREIGN PATENT DOCUMENTS

DE    43 41 722 A1    6/1994

(Continued)

*Primary Examiner*—Henry Bennett
*Assistant Examiner*—Shumaya B. Ali
(74) *Attorney, Agent, or Firm*—Workman Nydegger (57) ABSTRACT

A compression garment for compressing a portion of a body of a patient includes a tubular body. The body includes an outer layer and an inner layer secured to the outer layer. The inner layer at least partially bounds a channel adapted to receive a portion of a body of a patient. The inner layer includes a backing having a plurality of pressure projections extending therefrom. A layer of compressible cushioning material is disposed between the outer layer and the inner layer. Compression straps are disposed on the body for selectively constricting the body.

27 Claims, 8 Drawing Sheets

U.S. PATENT DOCUMENTS

| | | | |
|---|---|---|---|
| 4,971,041 A | 11/1990 | Millikan et al. | |
| 5,014,681 A | 5/1991 | Neeman et al. | |
| 5,063,910 A | 11/1991 | Cartier | |
| 5,171,211 A | 12/1992 | Deasy, Jr. | |
| 5,257,956 A | 11/1993 | Ewen | |
| 5,263,473 A | 11/1993 | McWhorter | |
| 5,403,265 A | 4/1995 | Berguer et al. | |
| 5,497,513 A | 3/1996 | Arabeyre et al. | |
| 5,591,121 A * | 1/1997 | Cantrell | 602/5 |
| 5,591,200 A | 1/1997 | Cone et al. | |
| 5,823,195 A | 10/1998 | Shook et al. | |
| 5,823,981 A * | 10/1998 | Grim et al. | 602/26 |
| 5,830,164 A | 11/1998 | Cone et al. | |
| 5,904,145 A | 5/1999 | Reid | |
| 5,916,183 A | 6/1999 | Reid | |
| 5,918,602 A | 7/1999 | Shaw et al. | |
| 5,976,099 A | 11/1999 | Kellogg | |
| 6,109,267 A | 8/2000 | Shaw et al. | |
| 6,179,796 B1 | 1/2001 | Waldridge | |
| 6,196,231 B1 | 3/2001 | Reid | |
| 6,224,564 B1 * | 5/2001 | Korobow | 602/62 |
| 6,254,554 B1 * | 7/2001 | Turtzo | 601/134 |
| 6,315,745 B1 | 11/2001 | Kloecker | |
| 6,338,723 B1 | 1/2002 | Carpenter et al. | |
| 6,401,247 B1 * | 6/2002 | Williams, IV | 2/59 |
| 6,436,064 B1 | 8/2002 | Kloecker | |
| 6,475,174 B1 * | 11/2002 | Chow | 602/5 |
| 6,482,167 B1 * | 11/2002 | Grim et al. | 602/8 |
| 6,508,776 B1 * | 1/2003 | Chiang et al. | 602/5 |
| 6,520,926 B1 * | 2/2003 | Hall | 602/64 |
| 6,551,280 B1 | 4/2003 | Knighton et al. | |
| 6,589,194 B1 | 7/2003 | Calderon et al. | |
| 6,592,539 B1 * | 7/2003 | Einarsson et al. | 602/62 |
| 6,645,165 B1 * | 11/2003 | Waldridge et al. | 601/152 |
| 6,656,141 B1 * | 12/2003 | Reid | 601/134 |
| 6,681,772 B1 * | 1/2004 | Atwater et al. | 128/878 |
| 6,700,031 B1 * | 3/2004 | Hahn | 602/41 |
| 6,808,501 B1 * | 10/2004 | Stess et al. | 602/6 |
| 2001/0018563 A1 | 8/2001 | Waldridge et al. | |
| 2002/0042585 A1 | 4/2002 | Kloecker | |
| 2003/0032905 A1 | 2/2003 | Waldridge et al. | |
| 2003/0045821 A1 | 3/2003 | Iker | |
| 2003/0125649 A1 | 7/2003 | McIntosh et al. | |

FOREIGN PATENT DOCUMENTS

| | | |
|---|---|---|
| EP | 0026799 B1 | 2/1985 |
| GB | 1 531 268 | 11/1978 |
| WO | WO 96/25108 | 8/1996 |

\* cited by examiner

COMPRESSION GARMENTS AND RELATED METHODS

CROSS-REFERENCE TO RELATED APPLICATIONS

Not applicable.

BACKGROUND OF THE INVENTION

1. The Field of the Invention

The present invention relates to compression garments and related methods or treating lymphedema and other forms of edema.

2. The Relevant Technology

Lymphedema is a chronic lifetime debilitation which is characterized by swelling in the arms and/or legs. This swelling is caused by the accumulation of lymphatic fluid in the extremities. Lymphedema is typically caused by either congenital-disruption of the normal lymphatic drainage system or by damage to the lymphatic drainage system. For example, lymphedema is often caused by the removal of lymph nodes which is due to the treatment of cancers such as breast cancer and lymphatic cancer.

Treating lymphedema and other forms of edema typically consists of a decongestive therapy wherein the unwanted fluid is initially drained from the extremity. Maintenance therapy is then used to prevent repeated accumulation of such fluid. Various forms of compression garments which apply an external compressive force to the patient's arms and/or legs have been used in the decongestive and maintenance therapies. While compression garments have met with some success, conventional compression garments have several shortcomings. For example, most approaches to the decongestive and maintenance therapies require a completely separate type of compression garment. Accordingly, such therapies have increased costs to the patient.

Furthermore, many compression garments are made of a thick foam material which is bulky and awkward to use, difficult to clean, and uncomfortable to wear in that it has poor breathability. Such bulky compression garments can also be emotionally uncomfortable in public in that they are highly conspicuous. Inflatable compression garments also suffer from lack of breathability and increased complexity. An additional problem with many compression garments is their poor ability to drain the unwanted fluid from the extremity.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

Figure 1:
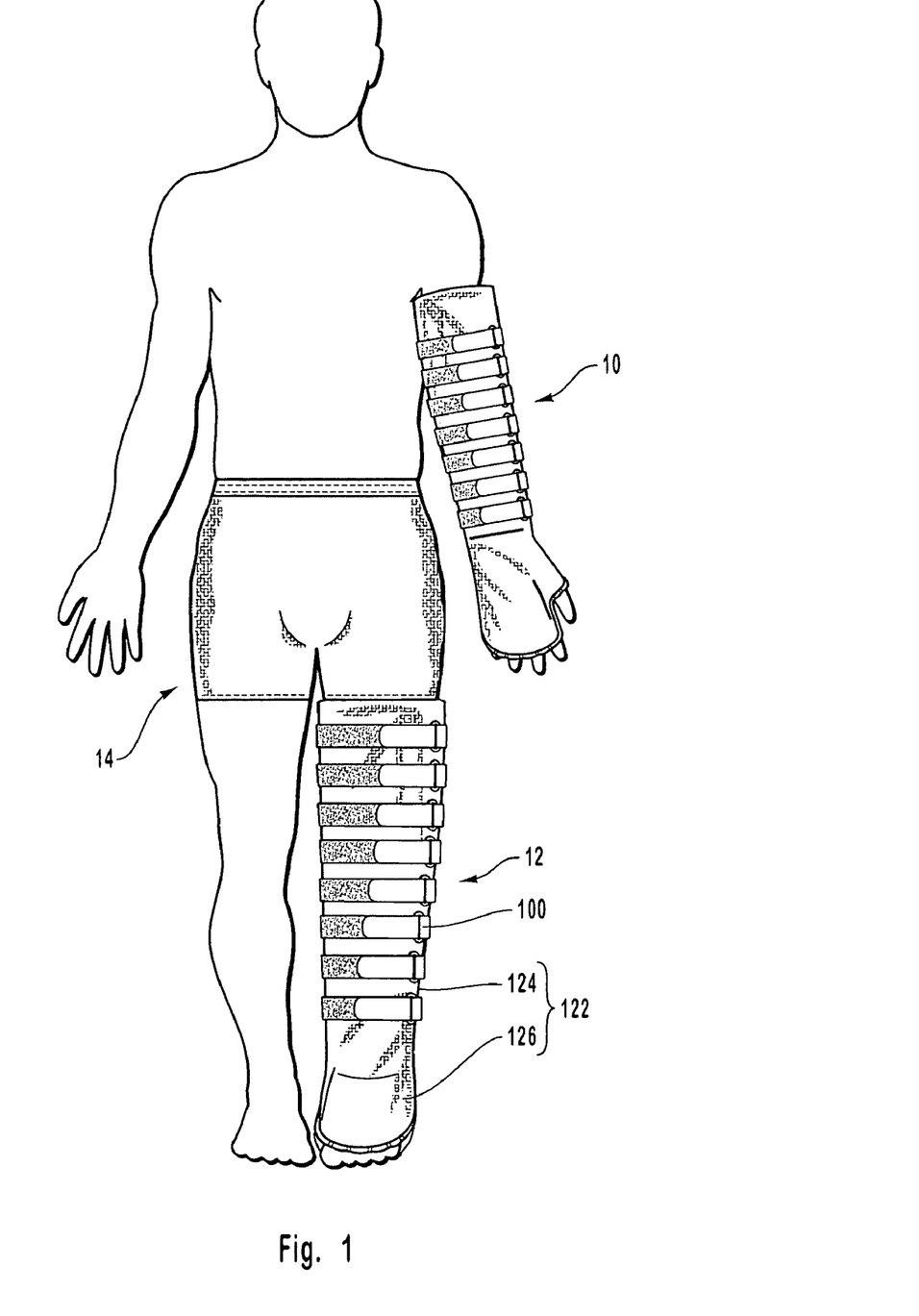
FIG. 1 is a front view of a patient having on various forms of compression garments.

The present invention relates to compression garments and related methods of use for treating lymphedema and other forms of edema. Depicted in FIG. 1 are embodiments of several different forms of pressure garments incorporating features of the present invention. Specifically, a compression garment 10 is shown for use over an arm and hand of a patient. Compression garment 12 is shown for use over a leg and foot of a patient. In alternative embodiments, compression garments 10 and 12 can be designed to only cover an arm or leg (i.e., not cover the hand or foot) or portions of an arm or leg. A compression garment 14 is also shown for use around the abdomen and groin area. It is likewise appreciated that compression garments can be formed for use over the chest area. In still other embodiments, compression garments can be formed to cover combined areas such as an arm and chest or leg and abdomen.

Figure 2:
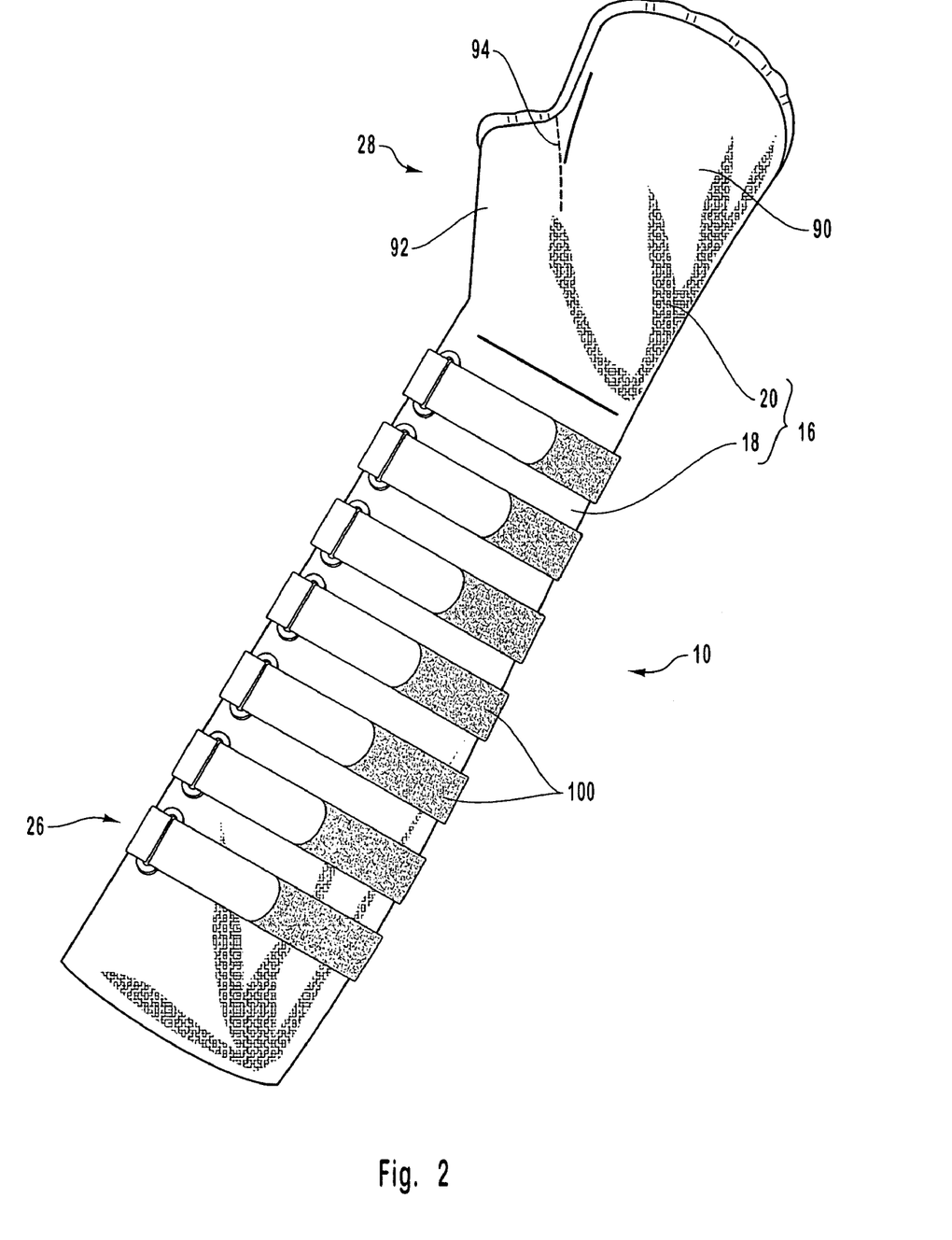
FIG. 2 is a top plan view of a compression garment used for an arm of a patient as shown in FIG. 1.
Figure 3:
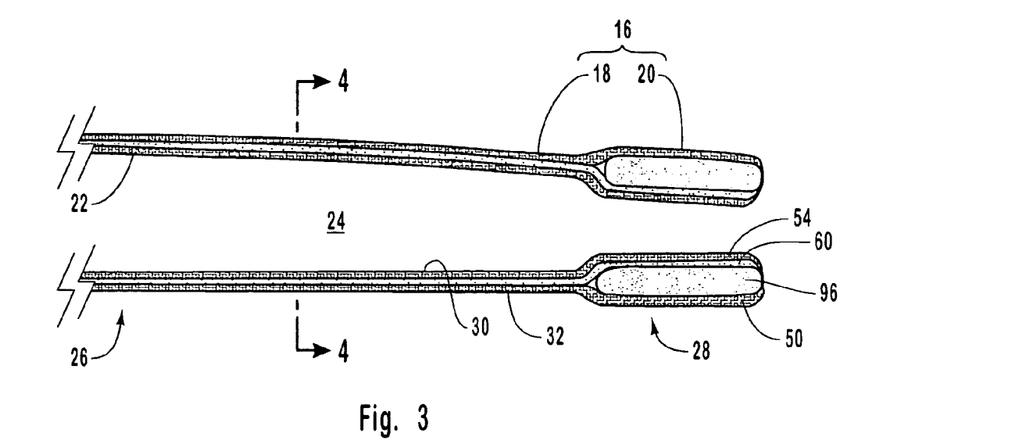
FIG. 3 is a longitudinal cross sectional side view of the body of the compression garment shown in FIG. 2.

Depicted in FIG. 2, compression garment 10 comprises an elongated body 16 having a plurality of compression straps 100 mounted thereon. As shown in FIGS. 2 and 3, body 16 has an interior surface 30 and an exterior surface 32 that each extend between a proximal end 26 and an opposing distal end 28. Interior surface 30 bounds a channel 24 extending along the length of body 16. Body 16 further comprises a tubular sleeve 18 configured to receive an arm of a patient and a substantially tubular hand portion 20 configured to at least substantially receive a hand of a patient. As depicted in FIG. 3, sleeve 18 has an interior surface 22 that bounds a portion of channel 24. Sleeve 18 is configured so that channel 24 radially inwardly tapers from proximal end 26 to toward distal end 28. This tapered configuration of channel 24 enables an arm of a patient to be received within channel 24 so that sleeve 18 produces a compressive force along the length of the arm. In one embodiment it is desired that the compressive force applied by sleeve 18 gradually increase proximal to distal. This helps to direct fluid back toward the chest. In other embodiments, the applied pressure can be substantially uniform.

Figure 4:
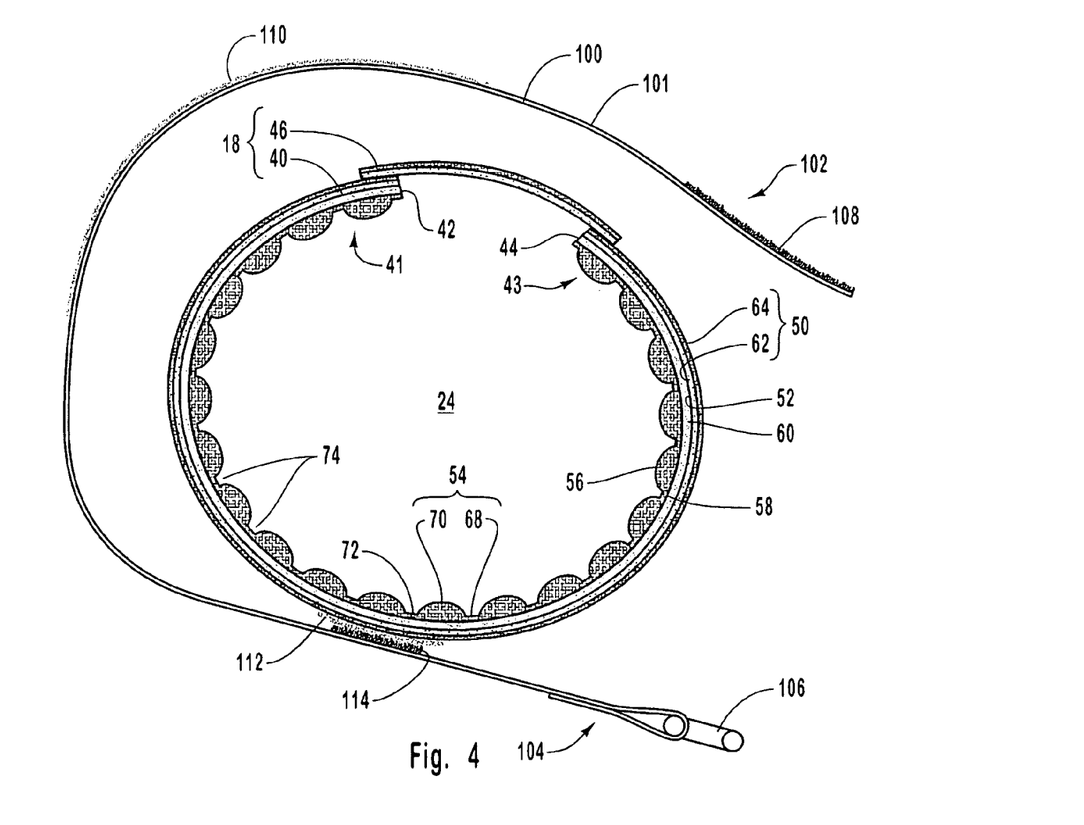
FIG. 4 is a transverse cross sectional side view of the body of the compression garment shown in FIG. 3 taken along lines 4—4.

In the embodiment depicted in FIG. 4, sleeve 18 comprises a flexible, substantially rectangular panel 40 having opposing sides 41 and 43. Sides 41 and 43 terminate at side edges 42 and 44, respectively. Panel 40 has been partially rolled so that edges 42 and 44 are adjacently disposed. Sleeve 18 further comprises an elongated, narrow bridge 46 which is secured to and extends between sides 41 and 43 along the length of panel 40. The combined panel 40 and bridge 46 forms tubular sleeve 18.

Panel 40 is further shown as comprising an outer layer 50 having an interior surface 52; an inner layer 54 having an interior surface 56 and an exterior surface 58; and an intermediate layer 60 disposed between outer layer 50 and inner layer 54. As with the other layers, outer layer 50 is typically comprised of a flexible, washable, and breathable material. Although outer layer 50 can comprise a single integral layer, in the embodiment depicted, outer layer 50 comprises an open cell polymeric foam layer 62 having a backing 64 secured by an adhesive over an outer surface thereof. Foam layer 62 typically has a thickness in a range between about 2 mm to about 15 mm with about 3 mm to about 7 mm being more common. Other dimension can also be used. Backing 64 is typically made of a breathable, washable fabric, such as cotton, woven nylon or the like. Other breathable materials such as perforated extruded sheets can also be used. Backing 64 provides an exposed, durable surface that can be resiliently stretchable or static. In one embodiment, outer layer 50 can comprise backing 64 without foam layer 62.

Intermediate layer 62 is comprised of a cushioning material that is typically flexible, washable, and breathable. One type of cushioning material is an open cell polymeric foam. Other cushioning materials that can be used include closed cell polymeric foam, conventional padding, and fabric padding such as the all in one moldable fabric produced by McMurray Fabric out of Lincolnton, N.C. Other materials can also be used. Intermediate layer 62 can comprise one or more layers that are either separate or combined. The one or more intermediate layers may or may not have backing. Intermediate layer 62 typically has a thickness in a range between about 2 mm to about 15 mm with about 3 mm to about 7 mm being more common. Although other dimension can also be used, it is generally desired to minimized the thickness of all foam layers so as to improve breathability and decrease bulk.

Figure 5A:
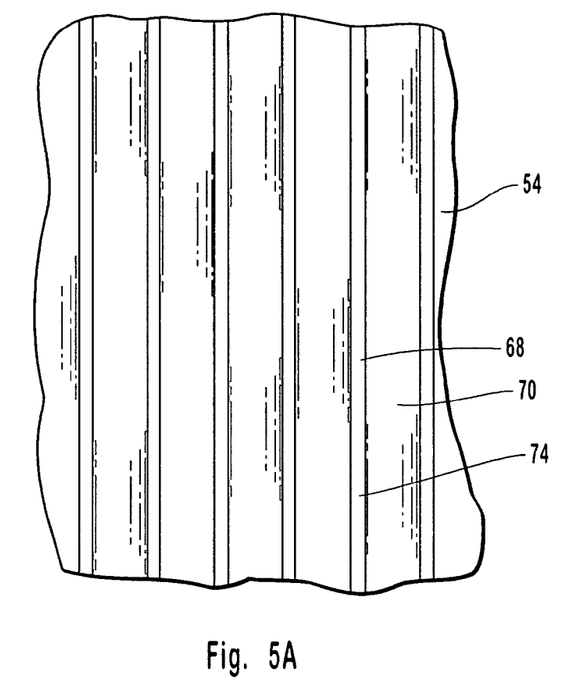
FIG. 5A is a top plan view of an inner layer of the compression garment shown in FIG. 4.

Inner layer 54 comprises a backing 68 having an interior surface 72. Backing 68 is typically flexible, washable, and breathable. Mounted on or projecting from interior surface 72 of backing 68 are a plurality of pressure projections 70. Pressure projections 70 are spaced apart or are otherwise formed so that recessed flow paths 74 are formed between or around pressure projections 70. For example, as depicted in FIG. 5A, inner layer 54 can be comprised of a convention corduroy or ribbed fabric wherein backing 68 comprises a base woven fabric layer and pressure projections 70 comprises piled fabric woven into the base layer so as to project therefrom in the form of linear rows. In alternative embodiments pressure projections 70 need not be in linear rows but can be curved, zigzagged, or any other desired configurations. Although corduroy is typically comprised of cotton, other fibers can also be used.

Figure 5B:
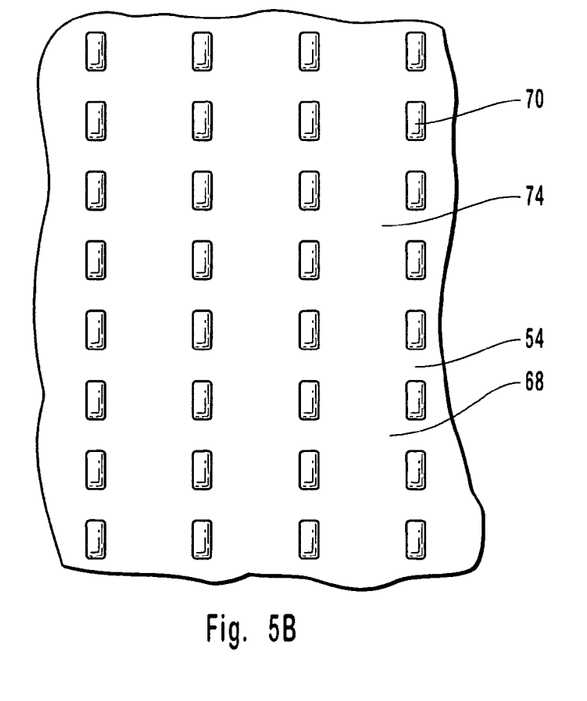
FIGS. 5B and 5C are top plan views of alternative embodiments of the inner layer shown in FIG. 5A.
Figure 5C:
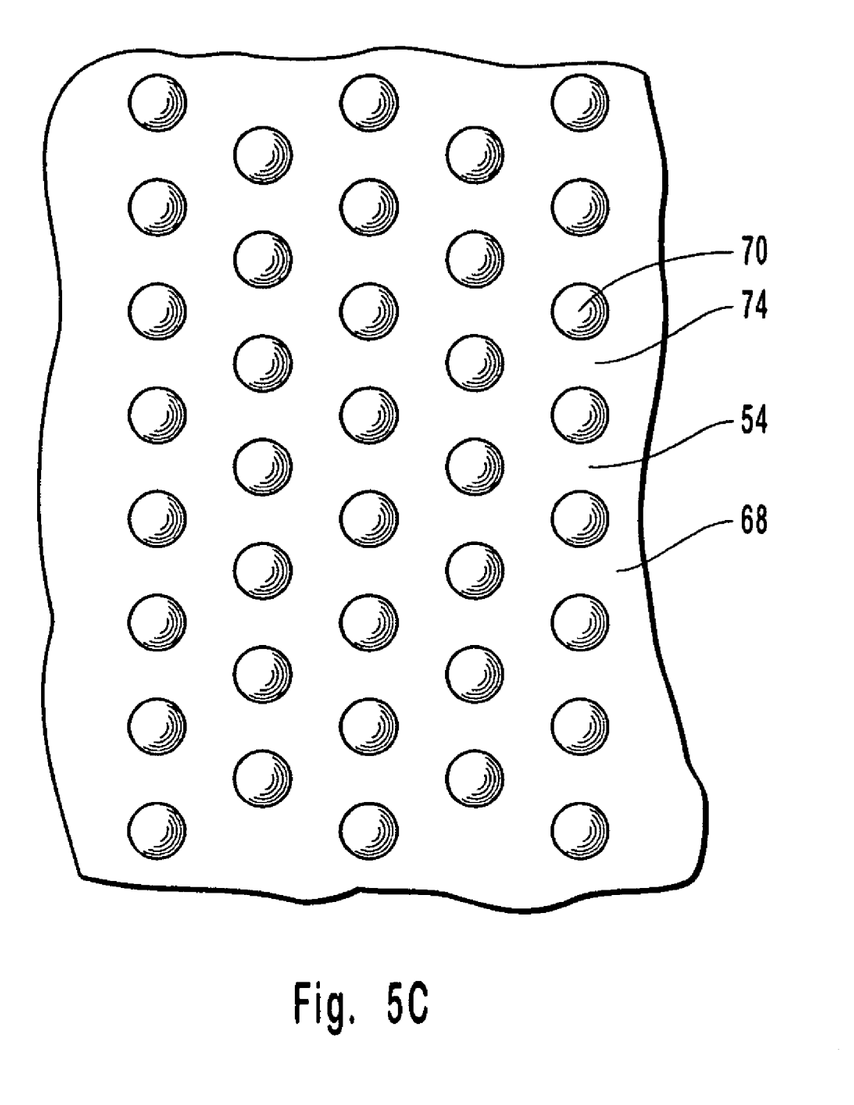

As depicted in FIG. 5B, pressure projections 70 need not be in the form of ribs but can comprise patches. The patches can be aligned as in FIG. 5B or randomly dispersed as depicted in FIG. 5C. Likewise, the patches can be any desired shape or size. In contrast to being a corduroy or corduroy type material wherein the backing 68 and pressure projections 70 are integrally woven together, it is also appreciated that the pressure projections 70 in rib, patch, or other configuration can be separately mounted onto backing 68 such as by stitching, tape, adhesive, Velcro, fastener, or the like. In these embodiments, backing 68 can comprise any breathable, woven fabric material or any other type of breathable material such as perforated polymeric sheets. Pressure projections 70 can be comprised of various materials such as linear and combed pile, brushed cotton or polymeric material, woven fabric, pillowed or quilted material, conventional padding, and fabric padding such as the all in one moldable fabric or the like. In yet other embodiments, pressure projections 70 can be comprised of rubber of jelled material such as silicone. Pressure projections 70 can also be comprised of inflatable bladders.

As will be discussed below in greater detail, pressure projections 70 are formed so that when sleeve 18 is received over an arm, pressure projections 70 form a plurality of localized high pressure areas on the arm separated by relative low pressure areas. As previously discussed, the low pressure areas are typically interconnected along the length of the arm so as to form flow paths 74 along the length of the arm. The general concept of the compression garment is that by apply extra pressure to the arm, the unwanted fluid naturally flows out of the arm toward the lower pressure area in the chest. It has been discovered, however, that by subjecting the arm to the high and low pressure areas, the unwanted fluid within the arm can more easily and quickly flow along the low pressure flow paths 74 toward the chest of the patient. This is in contrast to some conventional pressure garments wherein the garments apply a uniform high pressure over the entire surface of the arm. In these embodiments, the uniform high pressure applied over all surfaces of the arm can partially restrict the free flow of fluid out of the arm.

In one embodiment it is preferred that inner layer 54 or at least the portion thereof that directly contacts the surface of the arm of the patient not be made of a polymeric foam. The polymeric foam absorbs the oils and dirt from the arm and can be difficult to fully clean. Such foam is also less durable. Furthermore, because the polymeric foam is easily compressed, forming inner layer 54 out of polymeric foam so as to produce the high and low pressure areas requires inner layer 54, and particularly pressure projections 70, to have significantly increased thickness. Increasing the thickness of the foam, however, decreases breathability.

In contrast, by forming inner layer 54 out of corduroy or the other materials as discussed above, inner layer 54 can be easily cleaned. Furthermore, sleeve 18 can have a minimum thickness while still providing for high and lower pressure regions. For example, in one embodiment sleeve 18 has a thickness extending from interior surface 30 to exterior surface 32 in a range between about 0.5 cm to about 3 cm with about 0.5 cm to about 2 cm being more common. Other dimensions can also be used. As a result of having a minimum thickness, sleeve 18 is more convenient to use, i.e., is less bulky, has improved breathability making it more comfortable to wear, and is less conspicuous in public use. Sleeve 18 can also be easily cleaned by simply being washed in a conventional washing machine. Furthermore, as will be discussed below in greater detail, because of the low profile of sleeve 18, sleeve 18 can also be used in all treatment phases of the various forms of edema.

Figure 6A:
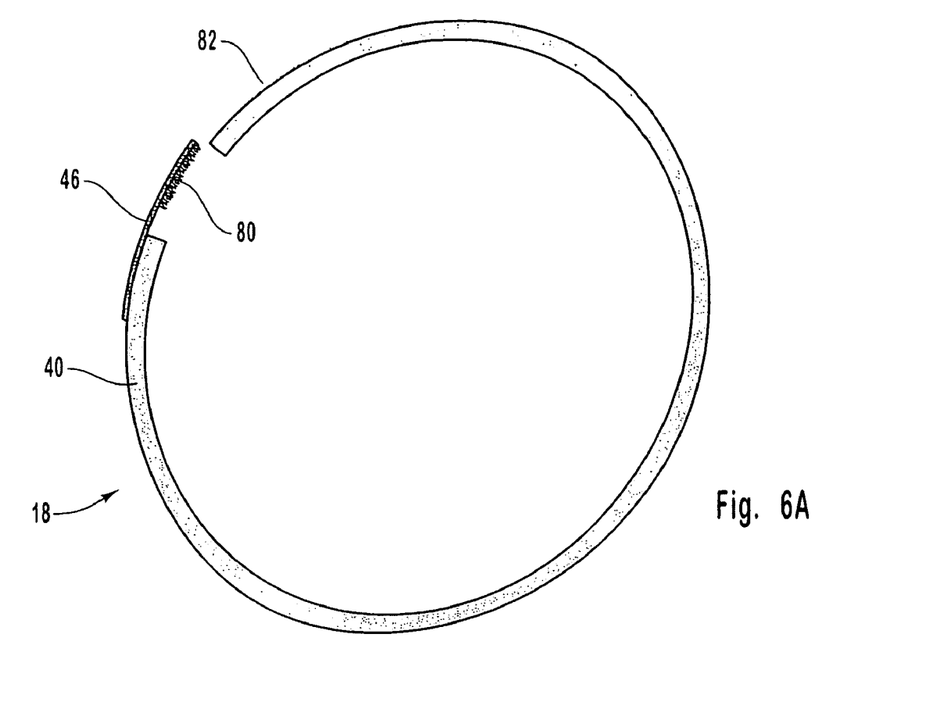
FIGS. 6A and 6B are transverse cross sectional side views of alternative embodiments of the body shown in FIG. 4.

Returning to FIG. 4, as previously mentioned bridge 46 is used to connect opposing edges 41 and 43 of panel 40. In one embodiment, bridge 46 comprises the same material as outer layer 50 of panel 40. Other materials can also be used. Such materials can be resiliently stretchable or static. In the embodiment in FIG. 4, bridge 46 is permanently attached to panel 40 such as by stitching, adhesive, seaming, or the like. In an alternative embodiment as depicted in FIG. 6A, a fastener can be mounted along one edge of bridge 46 so as to removably secure one or both edges of bridge 46 to panel 40. This enables panel 40 to be wrapped around the arm of the patient before it is secured in place. By way of example and not by limitation, Velcro can be used to secure bridge 46 and panel 40. Specifically, hook material 80 is mounted on bridge 46 while corresponding loop material 82 is mounted on the exterior of panel 40. In contrast to using Velcro, other fasteners such as button, snaps, hooks, clasps, ties, or any other fastener can be used.

Figure 6B:
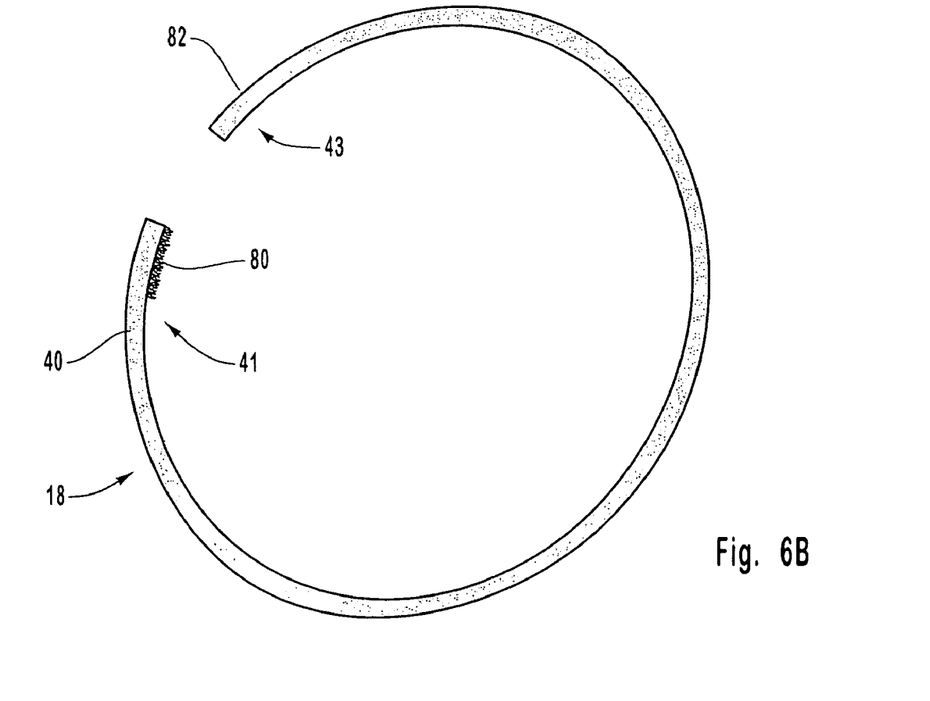

In yet other embodiments, it is appreciated that bridge 46 can be eliminated. For example, as depicted in FIG. 6B, a fastener can be used to directly connect edges 41 and 43 of panel 40. The fastener can comprise hooks 80 and loops 82 or any other alternative fasteners such as those discussed above. In still other embodiments, edges 41 and 43 can be permanently secured together such as by stitching, adhesive, seaming, or the like.

As depicted in FIG. 2, encircling sleeve 18 are a plurality of compression straps 100 which are closely staggered along the length of sleeve 18. Straps 22 can be selectively adjusted to constrict around sleeve 18 so as to selectively regulate the amount of pressure produced along the length of the arm of the patient. As depicted in FIG. 4, each compression strap 100 comprises a band 101 having a first end 102 and an opposing second end 104. Second end 104 loops through a D-ring 106 so that D-ring 106 is secured thereat. By passing first end 102 of band 101 through D-ring 106 and then pulling band 101 back over itself, band 101 constricts around sleeve so as to increase pressure on the arm of the patient. Once band 101 constricts to the desired extent, a fastener is used to hold band 101 in the desired position. For example, a hook material 108 and loop material 110, such as in conventional Velcro, can be mounted on band 101 for securing band 101 in the desired constriction. In alternative embodiments, other conventional fasteners such as pins, snaps, hooks, buttons, clips, ties, and the like can be used.

It is appreciated that compression straps 100 can come in a variety of different sizes, shapes, and configurations. Furthermore, compression straps 100 can function in a variety of different ways so as to selectively increase pressure on the arm. For example, the manually constricting straps can be replaced with one or more inflatable bladders that encircle the arm. By inflating the bladders, the pressure on the arm increases.

In the embodiment depicted, compression straps 100 can be selectively removed from sleeve 18 so that sleeve 18 can be used independent of compression straps 100. Although not required, to facilitate ease in mounting compression straps 100 on sleeve 100, a strip 112 of loop material is mounted along the length of sleeve 100. A complementary patch 114 of hook material is mounted on band 101 at or toward second end 104. By selectively pushing patch 114 against strip 112, compression strap 100 is releasably mounted to sleeve 18 to assist in subsequent use thereon. Again, strip 112 and patch 114 can be switched or replaced with any other conventional type of fastener such as pins, snaps, hooks, buttons, clips, ties, and the like.

Returning again to FIG. 2, as previously mentioned sleeve 18 can be formed and used without hand portion 20. In the embodiment depicted, however, hand portion 20 is integrally formed with or mounted on the distal end of sleeve 18. Hand portion 20 includes a tubular, substantially rectangular finger section 90 having a tubular thumb section 92 projecting off from a side thereof. A stitch line 94 separates finger section 90 from thumb section 92.

As discussed above, sleeve 18 is designed for use with compression straps 100. In contrast, hand portion 20 is designed to apply the desired pressure absent of any compression straps. Specifically, hand portion 20 includes outer layer 50, inner layer 54, and intermediate layer 60 as discussed above with regard to sleeve 18. In contrast to sleeve 18, however, a cushion layer 96 is disposed between intermediate layer 60 and outer layer 50. Cushion layer 96 can comprise any flexible, breathable, resiliently compressible material such as those discussed above with regard to intermediate layer 60. In one embodiment, compression layer 96 comprises a layer of open cell polymeric foam having a thickness in a range between about 4 mm to about 30 mm with about 7 mm to about 15 mm being more common. Other dimension can also be used. In contrast to being formed from a single layer, compression layer 96 can be comprised of two or more layers of the same of different material. It is also appreciated that intermediate layer 60 can be eliminated in hand portion 20 and the thickness of compression layer 96 increased.

As depicted in FIG. 3, by increasing the thickness of hand portion 20 relative to sleeve 18, the portion of channel 24 passing through hand portion 20 is further decreased. As a result, increased pressure is applied to the hand of a patient received within hand portion 20. As with sleeve 18, it is also desirable that the pressure applied by hand portion 20 gradually increase proximal to distal. Hand portion 20 is designed to apply sufficient pressure so that the unwanted fluid drains out of the hand without the application of compression straps 100 on hand portion 20. In one embodiment, hand portion 20 has a thickness extending from interior surface 30 to exterior surface 32 in a range between about 1 cm to about 4 cm with about 1.5 cm to about 3 cm being more common. Other dimensions can also be used.

Another unique benefit of the embodiment of compression garment 10 as depicted in FIGS. 1–4 is that the same garment can be used in multiple stages of the treatment of lymphedema and other forms of edema. For example, the treatment of lymphedema is typically a two stage process: decongestive phase and management phase. The decongestive phase is used to initially drain the unwanted fluid from the extremity. This is accomplished by applying a relatively high pressure to the extremity over a continuous and extended period of time. For example, in treating an arm of a patient, the arm is received within compression garment 10. Compression straps 100 are then selectively tightened with the pressure gradually increasing proximal to distal. Applied pressures are typically in a range between about 10 mm Hg to about 100 mm Hg. Other pressures can also be used. Depending on the severity of case, compression garment 10 is typically retained in this state for staggered intervals of about 72 hours during a 2–3 week period. During the decongestive phase, the unwanted fluid drains out of the arm by creating new drain paths within the arm.

Once the decongestive phase is over, the patient moves to the management phase where the applied pressures are lower and are applied at periodic intervals. For example, depending on the severity of the case, the applied lower pressures may need to be applied every 2–3 times a day, only at night, or only every couples of days. In one embodiment, compression straps 100 can again be used to apply the desired pressure during the management phase. Alternatively, compression straps 100 can be completely removed from sleeve 18 as discussed above.

Figure 7:
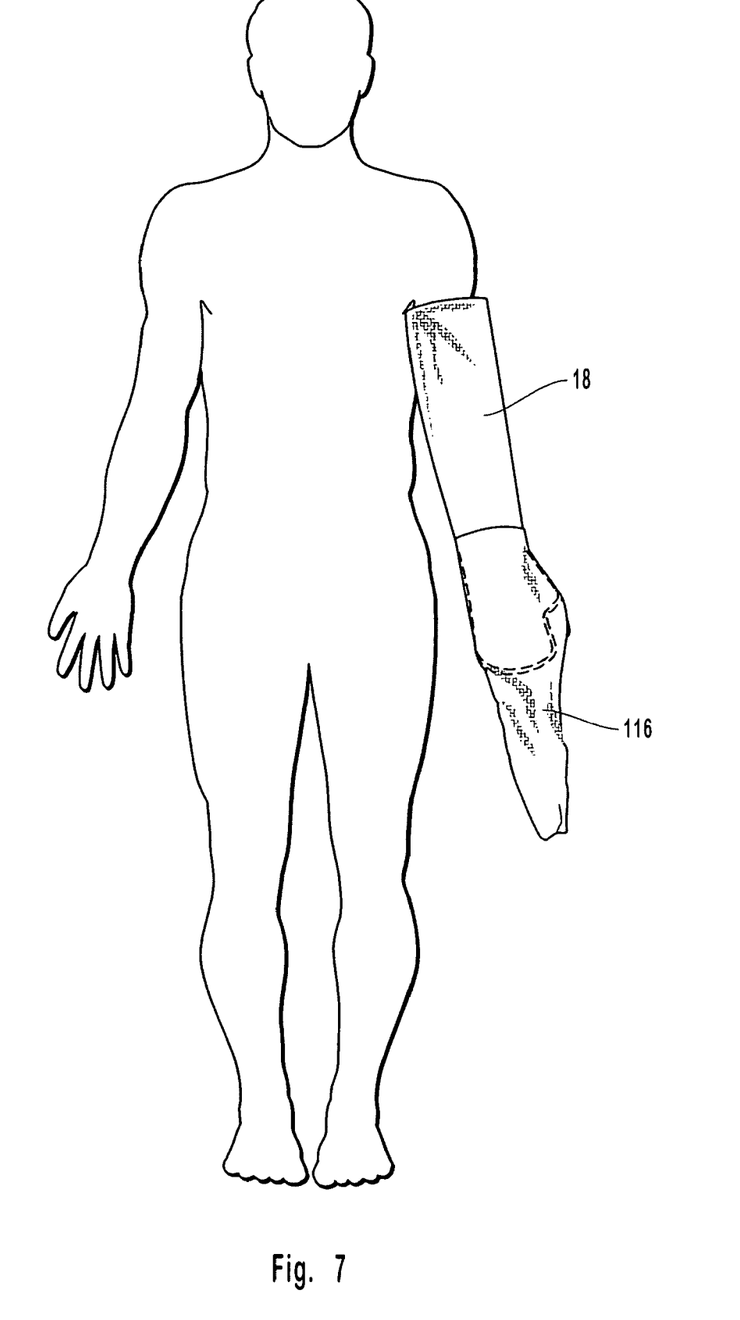
FIG. 7 is the front view of the patient shown in FIG. 1 wherein the compression straps of the compression garment are being replaced with a tubular sock.

Depicted in FIG. 7, once the compression straps 100 are removed, a tubular, resiliently stretchable sock 116 is stretched over sleeve 18. Sock 116 is typically open at both ends and is positioned so as to cover the entire length of sleeve 18 but not cover hand portion 20. In other embodiments, sock 116 can also cover hand portion 20. Sock 116 is designed so as to apply the desired pressure or pressures over the length of sleeve 18 so as to prevent the accumulation of fluid within the arm.

The use of sock 116 is typically preferred over compression straps 100 in the management phase in that sock 116 is less bulky, is easier to apply, is less conspicuous, and allows greater arm movement than compression straps 100. For example, because of the low profile of sleeve 18, sleeve 18 with sock 116 can be received within the arms of a suit coat or jacket so as to be worn without significant notice. Sock 116 is applied over sleeve 18, as opposed to being used independent of sleeve 18, because sleeve 18 provides some cushioning so that sock 116 does not kink and cut off blood flow when a patient bends his or her arm. Furthermore, sleeve 118 continues to produce high and lower pressure points on the skin so as to provide increase fluid flow as discussed above.

In view of the foregoing, because of the low profile design of sleeve 18, sleeve 18 can be used in both the intensive and management treatment phases of edema. This is beneficial over many conventional techniques which require two completely separate systems for the intensive and management treatment phases.

In one embodiment of the present invention, means are provided for constricting at least a potion of body 16 when body 16 is in the at least substantially tubular configuration. By way of example and not by limitation, corresponding structure that accomplishes such means includes sock 116, one or more compression straps 100, inflatable bladders, and alternatives to the foregoing as discussed herein.

Figure 8:
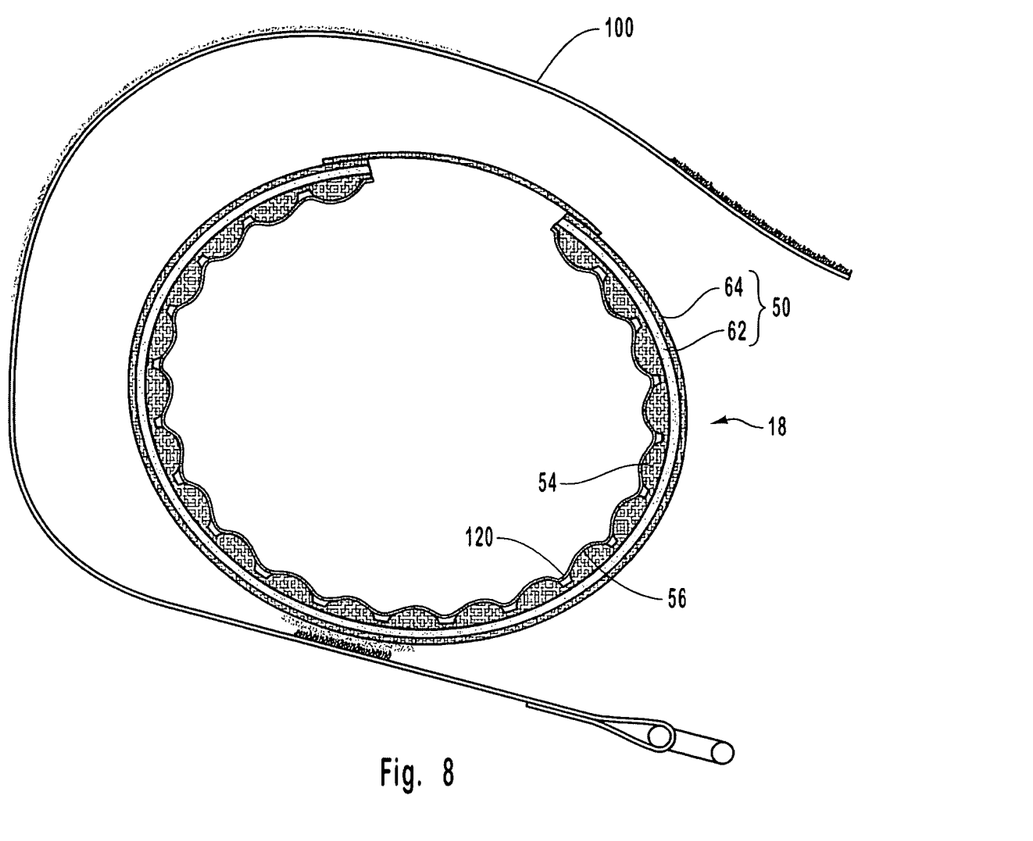
FIG. 8 is a transverse cross sectional side view of an alternative embodiment of the body shown in FIG. 4 having a different layer configuration.

Depicted in FIG. 8 is another alternative construction for sleeve 18. In this embodiment of sleeve 18 like elements are identified by like reference characters. As depicted, sleeve 18 comprises outer layer 50 having inner layer 54 mounted directly thereagainst. However, mounted on interior surface 56 of inner layer 54 is a cover layer 120. Cover layer 120 is comprised of a resiliently stretchable material such as Lycra or the like. Cover layer 120 helps to protect and keep clean inner layer 54. To assist in maintaining the pressure projections on inner layer 54, cover layer 120 is secured to inner layer 54 by resiliently stretching cover layer 120. Either before and/or after stretching cover layer 120, an adhesive is applied to an exterior surface of cover layer 120 and/or the interior surface of inner layer 54. Stretched cover layer 120 is then bonded to inner layer 54. Once the adhesive has set, the stretching force is released.

The above discussion was primarily directed to compression garment 10 as depicted in FIG. 1. It is appreciated, however that the same discussion is also applicable to compression garment 12 for use with a leg of a patient. For example, compression garment 12 comprises a body 122 which includes a tubular sleeve 124 to receive a leg of the patient and a foot portion 126 to receive a foot of a patient. Compression garment 12 can have the same alternative layers as compression garment 10 and can be used with compression straps 100 and sock 116. Although compression garment 14 can have the same structural alternatives as compression garment 10, it can be more difficult to apply compression straps 100 to compression garment 14. However, a sock 116 and/or inflatable bladder could be applied over compression garment 14.

The present invention may be embodied in other specific forms without departing from its spirit or essential characteristics. For example, compression garment 10 is discussed as having a number of different benefits. It is appreciated that a number of alternative embodiments of compression garment 10 can be made which include only one or combinations of the various benefits. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A compression garment for compressing a portion of a body of a patient, the compression garment comprising:
   a garment body comprising:
      an outer layer;
      an inner layer secured to the outer layer, the inner layer at least partially bounding a channel adapted to receive a portion of a body of a patient, the inner layer comprising:
         a backing comprising a woven fabric sheet or a perforated polymeric sheet having an interior surface facing the channel; and
         a plurality of spaced apart pressure projections extending from the backing toward the channel, the pressure projections being woven into the woven fabric sheet, the plurality of spaced apart pressure projections comprising a plurality of elongated ribs bounding a plurality of spaced apart recessed flow paths; and
      a layer of compressible cushioning material disposed between the outer layer and the inner layer.

2. A compression garment as recited in claim 1, wherein the garment body comprises a tubular sleeve adapted to receive an arm or leg of the patient.

3. A compression garment as recited in claim 1, wherein the inner layer comprises a corduroy fabric.

4. A compression garment as recited in claim 1, further comprising a cover layer mounted to the inner layer so as to directly cover the pressure projections.

5. A compression garment as recited in claim 4, wherein the cover layer comprises a sheet of resiliently stretchable material.

6. A compression garment as recited in claim 1, further comprising a plurality of compression straps secured to or encircling the garment body.

7. A compression garment as recited in claim 1, wherein the inner layer does not comprise a polymeric foam.

8. A compression garment as recited in claim 1, wherein the garment body has an interior surface and an exterior surface with a maximum non-compressed thickness extending therebetween in a range between about 0.5 cm and about 2 cm.

9. A compression garment as recited in claim 1, wherein the outer layer is comprised of a sheet of woven fabric material.

10. A compression garment for compressing at least a portion of an arm or a leg of a patient, the compression garment comprising:
   a body having a substantially tubular configuration or having the form of a panel that can be selectively rolled into a substantially tubular configuration, the body comprising:
      an outer layer;
      an inner layer secured to the outer layer, the inner layer at least partially bounding an elongated channel adapted to receive at least a portion of an arm or a leg of a patient, the inner layer comprising:
         a woven fabric sheet having an interior surface facing the channel; and
         plurality of spaced apart pressure projections extending from the fabric sheet toward the channel, the pressure projections comprising brushed cotton, a brushed polymeric material, woven fabric, or piled fabric secured on the fabric sheet, the plurality of spaced apart pressure projections bounding a plurality of spaced apart recessed flow paths; and a layer of resiliently compressible foam disposed between the outer layer and the inner layer; and means for constricting at least a portion of the body when the body is in the at least substantially tubular configuration.

11. A compression garment as recited in claim 10, wherein the pressure projections are woven into the woven fabric sheet.

12. A compression garment as recited in claim 11, wherein the inner layer comprises a corduroy fabric.

13. A compression garment as recited in claim 10, wherein the pressure projections are mounted onto to the woven fabric sheet.

14. A compression garment as recited in claim 10, wherein the pressure projections do not comprise polymeric foam.

15. A compression garment as recited in claim 10, further comprising a cover layer mounted on the inner layer so as to directly cover the pressure projections.

16. A compression garment as recited in claim 10, wherein the means for constricting at least a portion of the body comprises a plurality of compression straps secured to or encircling the garment body.

17. A compression garment as recited in claim 10, wherein the means for constricting at least a portion of the body comprises a resiliently stretchable tubular sock that is selectively pulled over the body.

18. A compression garment as recited in claim 10, wherein the body comprises:
 a tubular sleeve configured to receive an arm of the patient; and
 a tubular hand portion configured to receive a hand of the patient.

19. A compression garment as recited in claim 18, wherein the tubular sleeve has a thickness and the tubular hand portion has a thickness that is greater than the thickness of the tubular sleeve.

20. A compression garment system for compressing at least a portion of an arm or a leg of a patient, the compression garment system comprising:
 a body having a substantially tubular configuration or having the form of a panel that can be selectively rolled into a substantially tubular configuration, the body having an exterior surface and an opposing interior surface, the interior surface bounding a channel configured to receive at least a portion of an arm or a leg of a patient, the inner layer being comprised of a corduroy material;
 a plurality of compression straps removably disposed on the exterior surface of the body, each compression strap being configured to selectively constrict around the body when the body is in the substantially tubular configuration; and
 a tubular compression sock comprised of a resiliently stretchable material, the compression sock being configured to encircle at least a portion of the body when the body is in the substantially tabular configuration so as to radially inwardly compress the body when the compression straps are removed from the body.

21. A compression garment system as recited in claim 20, wherein the body comprises an outer layer secured to the inner layer, the outer layer comprising a sheet of woven fabric.

22. A compression garment system as recited in claim 21, further comprising a layer of polymeric foam disposed between the inner layer and the outer layer.

23. A compression garment for compressing at least a portion of an arm or a leg of a patient, the compression garment comprising:
 a body comprising:
  a sleeve having a substantially tubular configuration or having the form of a panel that can be selectively rolled into a substantially tubular configuration, the sleeve having an exterior surface and an opposing interior surface, the interior surface bounding a channel configured to receive at least a portion of an arm or a leg of a patient; and
  a terminal portion having a proximal end and a distal end mounted at an end of the sleeve, the terminal portion having an interior surface encircling a channel adapted to receive a band or foot of the patient, the terminal portion being configured to apply progressive pressure along the length of the hand or the foot when received therein without the use of an external pressure force, wherein the progressive pressure increases the pressure from the proximal end to the distal end of the terminal portion, the body having an inner layer comprised of a corduroy material; and
 a means for constricting at least a portion of the body, the means for constricting comprising:
  a plurality of compression straps connected to or removably disposed on the exterior surface of the sleeve, each of the compression straps being configured to selectively constrict around the sleeve when the compression sleeve is in the substantially tubular configuration; or
  a tubular compression sock comprised of a resiliently stretchable material that can be selectively pulled over the body.

24. A compression garment as recited in claim 23, wherein no compression straps are mounted on or encircle the terminal portion of the body.

25. A compression garment as recited in claim 23, wherein the body comprises an outer layer secured to the inner layer, the outer layer comprising a sheet of woven fabric.

26. A compression garment as recited in claim 25, further comprising a layer of polymeric foam disposed between the inner layer and the outer layer.

27. A compression garment as recited in claim 1, further comprising a tubular compression sock comprised of a resiliently stretchable material that can be selectively pulled over the garment body.

* * * * *

UNITED STATES PATENT AND TRADEMARK OFFICE
CERTIFICATE OF CORRECTION

PATENT NO. : 7,135,007 B2 Page 1 of 1
APPLICATION NO. : 10/719407
DATED : November 14, 2006
INVENTOR(S) : Scott et al.

It is certified that error appears in the above-identified patent and that said Letters Patent is hereby corrected as shown below:

Column 3
Line 6, change "dimension" to --dimensions--
Line 14, change "62" to --60--
Line 21, change "62" to --60--
Line 24, change "62" to --60--
Line 26, change "dimension" to --dimensions--
Line 38, change "convention" to --conventional--

Column 4
Line 9, change "apply" to --applying--

Column 5
Line 40, after "sleeve" change "100" to --18--
Line 41, change "100" to --18--

Column 6
Line 6, after "same" change "of" to --or--
Line 16, change "increase" to --increases--
Line 49, change "couples" to --couple--

Column 7
Line 7, change "118" to --18--
Line 8, change "increase" to --increased--

Signed and Sealed this

Fourteenth Day of August, 2007

JON W. DUDAS
*Director of the United States Patent and Trademark Office*